(12) United States Patent
Roper et al.

(10) Patent No.: US 8,790,596 B2
(45) Date of Patent: Jul. 29, 2014

(54) DISPENSER WITH FILTER DEVICE

(75) Inventors: Philip G. Roper, Tucson, AZ (US); Kevin Talucci, Tucson, AZ (US); Shane Rowland, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/485,798

(22) Filed: May 31, 2012

(65) Prior Publication Data

US 2012/0308445 A1    Dec. 6, 2012

Related U.S. Application Data

(60) Provisional application No. 61/492,322, filed on Jun. 1, 2011.

(51) Int. Cl.
*B67D 7/76* (2010.01)
*B01L 3/02* (2006.01)

(52) U.S. Cl.
USPC ..................................... 422/513; 222/189.06

(58) Field of Classification Search
CPC ................. G01N 2035/1053; B01L 2300/0681
USPC ........................................................ 422/513
See application file for complete search history.

(56) References Cited

U.S. PATENT DOCUMENTS

| | | | |
|---|---|---|---|
| 2,234,079 A | 3/1941 | Miller | |
| 3,650,437 A | 3/1972 | Binnings et al. | |
| 3,695,281 A | 10/1972 | Leon | |
| 3,726,442 A | 4/1973 | Davidson et al. | |
| 3,795,149 A | 3/1974 | Gillette et al. | |
| 3,854,703 A | 12/1974 | Gibbs et al. | |
| 4,126,558 A | 11/1978 | Luceyk | |
| 4,298,358 A | 11/1981 | Ruschke | |
| 4,362,977 A | 12/1982 | Evans et al. | |
| 4,455,280 A | 6/1984 | Shinohara et al. | |
| 4,533,475 A | 8/1985 | Chiarito | |
| 4,783,318 A | 11/1988 | Lapakko | |
| 4,964,544 A | 10/1990 | Hanna et al. | |
| 4,971,913 A | 11/1990 | Manabe et al. | |
| 5,120,438 A * | 6/1992 | Nakagawa et al. | ........... 210/256 |
| 5,232,664 A | 8/1993 | Krawzak et al. | |

(Continued)

FOREIGN PATENT DOCUMENTS

| | | |
|---|---|---|
| EP | 2425884 A1 * | 3/2012 |
| FR | 2541244 A1 | 8/1984 |

(Continued)

OTHER PUBLICATIONS

International Search Report and Written Opinion: International Patent Application No. PCT/EP2012/060197: Applicant Ventana Medical Systems, Inc.: mailed Sep. 17, 2012:13 pages.

*Primary Examiner* — Jill Warden
*Assistant Examiner* — Brittany Fisher
(74) *Attorney, Agent, or Firm* — Perkins Coie LLP

(57) ABSTRACT

A biological processing system includes a platform assembly for holding slides and a dispenser assembly with dispensers. The dispensers are sequentially positionable over specimen-bearing slides to enable dispensing of substances onto specimens. The dispensers include a filter device for filtering a processing substance such that a substantially precipitate-free filtrate is applied to the specimens. The dispenser includes a filter device positioned at least partially in a reservoir chamber. The filter device includes anti-clogging features to maintain desired performance.

23 Claims, 12 Drawing Sheets

(56) References Cited

U.S. PATENT DOCUMENTS

| | | |
|---|---|---|
| 5,289,385 A | 2/1994 | Grandone |
| 5,314,825 A | 5/1994 | Weyrauch et al. |
| 5,316,726 A | 5/1994 | Babson et al. |
| 5,348,705 A | 9/1994 | Koreyasu et al. |
| 5,373,972 A | 12/1994 | Bystrom et al. |
| 5,417,356 A | 5/1995 | Franklin et al. |
| 5,418,138 A | 5/1995 | Miller et al. |
| 5,425,918 A | 6/1995 | Healey et al. |
| 5,428,470 A | 6/1995 | Labriola, II |
| 5,431,309 A | 7/1995 | Ophardt |
| 5,439,646 A | 8/1995 | Tanimizu et al. |
| 5,443,791 A | 8/1995 | Cathcart et al. |
| 5,445,288 A | 8/1995 | Banks |
| 5,446,652 A | 8/1995 | Peterson et al. |
| 5,474,541 A | 12/1995 | Ritsky et al. |
| 5,474,744 A | 12/1995 | Lerch |
| 5,507,417 A | 4/1996 | Webb |
| 5,573,727 A | 11/1996 | Keefe |
| 5,595,326 A | 1/1997 | Bougamont et al. |
| 5,595,707 A | 1/1997 | Copeland et al. |
| 5,650,327 A | 7/1997 | Copeland et al. |
| 5,654,199 A | 8/1997 | Copeland et al. |
| 5,654,200 A | 8/1997 | Copeland et al. |
| 5,687,882 A | 11/1997 | Mueller |
| 5,695,718 A | 12/1997 | Imai et al. |
| 5,779,674 A | 7/1998 | Ford |
| 5,860,456 A | 1/1999 | Bydlon et al. |
| 5,961,492 A | 10/1999 | Kriesel et al. |
| 6,045,759 A | 4/2000 | Ford et al. |
| 6,093,574 A | 7/2000 | Druyor-Sanchez et al. |
| 6,119,766 A | 9/2000 | Blomgren |
| 6,192,945 B1 | 2/2001 | Ford et al. |
| 6,207,052 B1 * | 3/2001 | Webb ...................... 210/321.75 |
| 6,416,713 B1 | 7/2002 | Ford et al. |
| 6,851,583 B2 * | 2/2005 | Masuzzo et al. ........... 222/321.6 |
| 6,945,128 B2 | 9/2005 | Ford et al. |
| 7,040,511 B1 * | 5/2006 | Petit ........................ 222/189.09 |
| 7,225,931 B2 | 6/2007 | Glad |
| 7,946,455 B2 * | 5/2011 | Ritsche et al. ............. 222/321.6 |
| 8,279,434 B2 | 10/2012 | Mertsching et al. |
| 2002/0110494 A1 | 8/2002 | Lemme et al. |
| 2005/0135972 A1 * | 6/2005 | Lemme et al. ................ 422/100 |
| 2005/0189286 A1 | 9/2005 | Ferguson |
| 2005/0195684 A1 * | 9/2005 | Mayer ........................... 366/197 |
| 2009/0127183 A1 | 5/2009 | Lauer |

FOREIGN PATENT DOCUMENTS

| | | |
|---|---|---|
| WO | WO-92/04004 A1 | 3/1992 |
| WO | WO-2005/000731 A2 | 1/2005 |
| WO | WO 2010124633 A1 * | 11/2010 |
| WO | WO-2012/163992 A1 | 12/2012 |

* cited by examiner

DISPENSER WITH FILTER DEVICE

CROSS-REFERENCE TO RELATED APPLICATION

This patent application claims the benefit of U.S. Provisional Patent Application Ser. No. 61/492,322 entitled "DISPENSER WITH FILTER DEVICE" filed on Jun. 1, 2011, the contents of which are incorporated herein by reference in its entirety.

BACKGROUND

1. Technical Field

The invention relates generally to methods and apparatuses for biological processing systems. More specifically, the invention relates to dispensers with filter devices.

2. Description of the Related Art

Automated biological processing systems can process samples for immunostaining and in situ DNA analysis. Immunostaining and in situ DNA analysis are useful tools in histological diagnosis and the study of tissue morphology. Immunostaining relies on the specific binding affinity of antibodies with epitopes in tissue samples, and the increasing availability of antibodies which bind specifically with unique epitopes present only in certain types of diseased cellular tissue, immunostaining involves delivering a series of substances to a tissue section mounted on a glass slide to highlight, by selective staining, certain morphological indicators of disease states. Typical processing steps include pretreatment of the tissue section to reduce non-specific binding, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. A secondary anti-antibody can bind to the primary antibody that also includes a signal generating moiety such as an enzyme (for example, horseradish peroxidase or alkaline phosphatase) conjugated thereto. A combination of antibody conjugates that specifically bind the primary and the secondary antibodies is applied to the specimen. A DAB regent (e.g., diaminobenzidine (DAB)/hydrogen peroxide solution) is contacted to the specimen and allowed to incubate, during which time enzymes of the secondary antibody conjugate converts the soluble DAB into an insoluble brown precipitate at the sites where the primary antibody is specifically bound. The specimen is washed with buffer, followed by one or more rinses with ethanol, and one or more rinses with limonene to ready the specimen for subsequent processing, such as coverslipping.

Conventional automated biological processing systems often include dispensers that sequentially deliver fluids onto specimens. The dispensers can selectively dispense predetermined volumes of reagent. If solid particles (e.g., contaminates precipitates, or the like) are present in the fluid held in the dispensers, the solid particles may lead to impaired performance of the dispenser valving which results in improper dispensing. By way of example, if large precipitates form in a stored reagent, the precipitates can prevent complete closing of a valve. Conventional dispensers often hold precipitate forming solutions that tend to contain relative large precipitates (e.g., solid particles with diameters equal to or larger than about 0.01 inch), especially if the dispenser is stored for extended periods of time.

BRIEF SUMMARY

At least sortie biological processing systems include a platform assembly for holding slides and a dispenser assembly with dispensers. The dispensers can be sequentially positioned over specimen-bearing slides to enable dispensing of substances onto the specimens. The dispensers include filter devices for filtering processing substances to deliver substantially precipitate-free filtrate onto the specimens.

In certain embodiments, one of the dispensers includes a barrel with a main body and a piston. A valve is positioned downstream of a reservoir chamber defined by the main body. The filter device is positioned at the bottom of the reservoir chamber. If solid particles are in the chamber, the filter device can prevent solid particles larger than a threshold size from accessing and clogging fluidic components. The solid particles can be precipitate that separates from a solution or suspension by a chemical or physical change. Additionally or alternatively, the solid particles can be contaminates from the surrounding environment.

The filtering element includes through-holes with inlets positioned closer to a longitudinal axis of the filter device than an outer periphery of a protective cantilevered member positioned above the filtering element. In certain embodiments, the protective cantilevered member is part of a circular disk shaped portion of the filter device. The protective cantilevered member can also be in the form of an arcuate flange.

In some embodiments, a biological processing system includes a platform assembly and a dispenser assembly. The platform assembly includes slide holders. The dispenser assembly includes dispensers and is configured to cooperate with the platform assembly to sequentially position the dispensers relative to specimen-bearing slides on the slide holders so as to enable dispensing of substances onto the specimens. One or more of the dispensers includes a filter device capable of filtering a substance to deliver a substantially precipitate-free filtrate through components of the dispenser assembly.

The substantially precipitate-free filtrate can be a fluid that has solid particles, if any, with an outer diameter smaller than a threshold diameter. In certain embodiments, substantially precipitate-free filtrate is substantially free of all solid particles having an outer diameter larger than about 0.01 inch. Other threshold diameters or dimensions are also possible.

The filter element can be a longitudinally-extending perforated sidewall. In some embodiments, the perforated sidewall comprises a substantially flat member with a plurality a through-holes. In other embodiments, the perforated sidewall can be curved.

Dispensers can include a barrel holder and a barrel guided within (e.g., slidably coupled to) the barrel holder. The barrel includes a main body and a piston coupled to the main body. The main body defines a reservoir chamber for holding a fluid to be dispensed. A filtering element of a filter device can be submerged in the fluid and is configured to allow fluids to pass therethrough while substantially blocking precipitates of a threshold size from exiting the barrel. In certain embodiments, the filtering element includes one or more perforated plates, membranes, screens, meshes, or combinations thereof.

In yet other embodiments, a dispenser includes a barrel, a valve, and a filter device. The barrel includes a main body that defines a reservoir chamber for holding fluid. The valve is positioned downstream of the reservoir chamber. The filter device includes a filtering element that allows fluid in the reservoir chamber to pass through the filter device towards the valve while blocking at least some precipitates, or other solid particles in the fluid. In certain embodiments, the main body and a piston, which is downstream of the filter device, have a one-piece construction. In other embodiments, the main body and piston have a multi-piece construction.

One or more anti-clogging elements can help keep precipitates from reaching the filtering element in certain embodiments, anti-clogging elements are connected to a hollow main body of the filter device. For example, anti-clogging elements can extend outwardly from the main body a sufficient distance to help keep precipitates from reaching the filtering element.

In yet further embodiments, a filter device includes a hollow main body defining an outlet port and a filtering element. The filtering element can be configured to substantially block precipitates in a chamber of a reagent dispenser in which the filter device is installed. A filtering element allows reagents to flow through the filtering element, the hollow body, and the outlet port.

A filtering element, in some embodiments, can include a longitudinally-extending perforated wall extending along the length of a filtering element. In one embodiment, a pair of spaced apart longitudinally-extending perforated sidewalls allow reagent to flow into the hollow main body. The filter device can include one or more particle blockers. An upper particle blocker and a lower particle blocker can protrude outwardly from the main body to define a substantially horizontally flow channel through which fluid is capable of flowing to access the filtering element. The particle blockers can function as anti-clogging features.

Dispensers with filtering capabilities can be used in different types of equipment capable of conditioning specimens, staining specimens, performing antigen retrieval, performing immunohistochemistry (IHC), and/or performing in situ hybridization (ISH), as well as other processes for preparing specimens for microscopy, micro-analyses, mass spectrometric methods, or the like. The specimens can be in the form of biological samples (e.g., samples of tissue such as sections of an organ, tumor sections, bodily fluids, smears, frozen sections, cytology preparations, or cell lines). Tissue can be any collection of cells mountable on a slide.

In yet further embodiments, a filter device includes a hollow main body and means for filtering fluid to substantially block precipitates in a chamber of a dispenser while allowing fluid in the dispenser to flow through the hollow main body. In certain embodiments, the filter device further includes means for inhibiting clogging of the means for filtering. The means for filtering can include a perforated side all, screen, mesh, or combinations thereof. The means for inhibiting clogging can include one or more protrusions (e.g., cantilevered members) configured to inhibit movement of solid particles in the fluid.

In some embodiments, a filter device includes one or more recessed regions through which fluid flows. The recessed regions can be laterally offset perforated sidewalls. The main body of the filter device can have protrusions that extend outward past through-holes in the perforated wall.

BRIEF DESCRIPTION OF THE SEVERAL VIEWS OF THE DRAWINGS

Non-limiting and non-exhaustive embodiments are described with reference to the following drawings. The same reference numerals refer to like parts or acts throughout the various views, unless otherwise specified.

DETAILED DESCRIPTION

Figure 1:
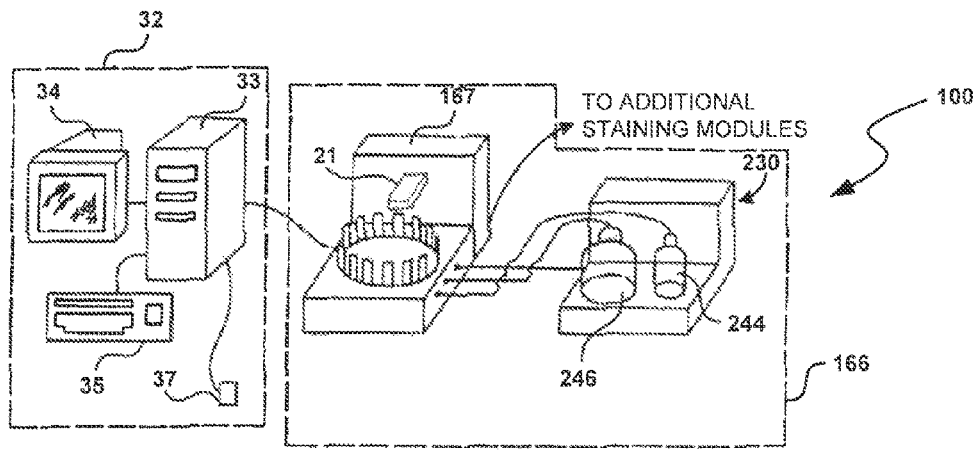
FIG. 1 is a left, front, and top isometric view of an automated biological processing system according to one embodiment.

FIG. 1 shows an automated biological processing system 100 including a host device 32 and a remote device 166. The remote device 166 includes a staining module 167 and a bulk fluid module 230. The host device 32 includes a host computer 33, a monitor 34, a keyboard 35, and a mouse 37. The host device 32 commands the staining module 167 to deliver a set of fluids from an array of dispensers to process specimens on microscope slides in the staining module 167. After processing, the slides can be removed from the staining module 167 for examination or subsequent processing.

Figure 2:
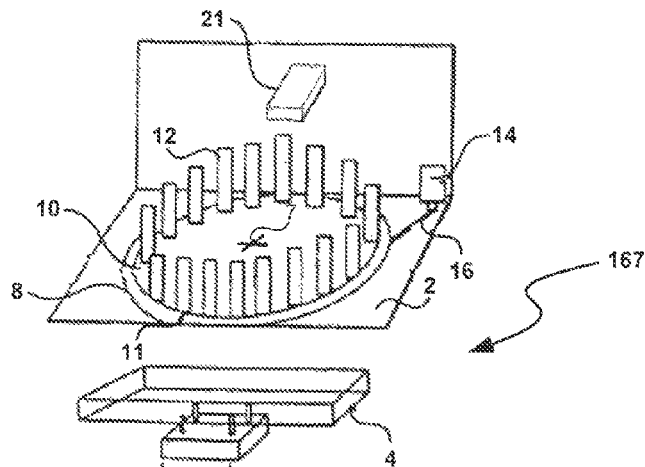
FIG. 2 is an exploded right, front, and top isometric view of the biological processing system of FIG. 1.
Figure 2:
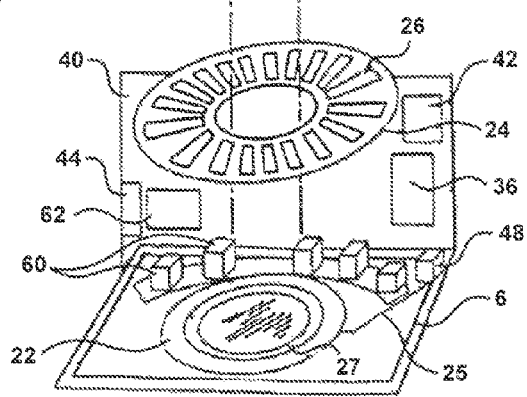

Referring to FIGS. 1 and 2, staining module 167 is capable of performing different protocols. The dispensers 12 can be conveniently replaced to perform different protocols or when emptied and can be stored for extended lengths of time, as well as subjected to extreme operating conditions (e.g., high temperatures) without adversely effecting performance because internal filter devices can keep particles or other unwanted material carried in the fluid from reaching fluidic components.

A lab may have a supply of dispensers to perform different types of protocols. The shelf life of conventional dispensers can be relatively short because precipitate forming reagents may lead to dispenser malfunction. Malfunctioning dispensers can result in inconsistent specimen processing and, in some instances, inoperability of a dispenser. Inconsistent processing can result in undesired staining that may not provide sufficient contrast. Filtering can alleviate or eliminate these type of problems often associated with conventional staining systems.

Advantageously, staining module 167 can include dispensers that filter reagents to ensure proper functioning, even after the dispensers are stored for a significant length of time. By way of example, DAB reagents can be a substrate solution used to provide contrast of enzyme activity. Internal filters within fluid containers ensure that filtrate outputted from the DAB dispenser does not contain precipitates sufficiently large to impair performance of downstream components. DAB reagents are also used to deposit a brown stain in the presence of another reagent, such as horseradish peroxidase (HRP) and is used in immunohistochemical and immunoblotting applications. Chromophore reagents can be in the form of solutions that comprise oxidoreductases such as horseradish peroxidase and a substrate such as diaminobenzidine (DAB) and amino-ethyl carbozole (AEC) which yields a distinguishing color (brown and red, respectively). A chromophore reagent set of dispensers can include dispensers filled with buffers, a DAB solution, and peroxide solution. Precipitate comprising DAB sulfate can form in DAB dispenser and can be captured to avoid impaired performance of the staining module 167.

In some setups, staining module 167 performs immunochemical staining protocols. Exemplary immunochemical staining protocols can include dispensing a rinsing solution (e.g., a solution comprising water and a detergent) to wash an assay region of a slide (the region containing the tissue section). An evaporation inhibitor liquid can be applied to cover the assay region. For antigens requiring unmasking, the tissue section is combined with a stabilized proteolytic enzyme solution. The slide is rinsed, and the evaporation inhibitor liquid is reapplied to the slide. A primary antibody in diluent containing globulins from the same species as a second antibody is combined with the tissue section for a time sufficient for substantially complete antibody binding. The slide is rinsed and the evaporation inhibitor liquid is reapplied. A labeled second antibody is applied to the tissue section for a time sufficient for substantially complete antibody binding. The slide is rinsed and the evaporation inhibitor liquid is reapplied to the slide. Color development reagents, including a stabilized peroxidase chromophore formulation, are combined with the tissue section for a time sufficient for color development. The stabilized peroxidase chromophore formulation comprises a peroxidase chromophore (at a concentration in the working range of the enzyme) an acidic buffer, a reducing agent, and a glycol. Chromophores can include 3,3'-diaminobenzidine and tetrahydrochloride (DAB) and 3-amino-9-ethylcarbazole (AEC). After color development, the tissue section is washed and ready for coverslipping. Each of the different liquids can be dispensed from a different dispenser.

Referring to FIG. 2, staining module 167 includes a dispenser assembly 2, an intermediate section 4, and a platform assembly 6. The dispenser assembly 2 can include a reagent tray 10 that supports dispensers in the form of fluid dispensers 12. Dispensers 12 can be supported by the reagent tray 10 and, in some embodiments, mounted in reagent fluid dispenser receptors 11 rotatable about a central axis 7 using a rotatable carousel 8.

Dispensers 12 can be capable of selectively dispensing desired volumes of fluids (e.g., gases, liquids, or gas/liquid mixtures) onto specimen-bearing slides carried on slide supports 26. The dispensed fluids can be, without limitation, reagents, probes, rinses, and/or conditioners and can include solvents (e.g., polar solvents, non-polar solvents, etc.), solutions (e.g. aqueous solutions or other types of solutions), or the like. Reagents include, without limitation, stains, wetting agents, antibodies (e.g., monoclonal antibodies, polyclonal antibodies, etc.), antigen recovery fluids (e.g., aqueous- or non-aqueous-based antigen retrieval solutions, antigen recovery buffers, etc.), or the like. Stains include, without limitation, dyes, hematoxylin stains, eosin stains, conjugates of antibodies or nucleic acids with detectable labels such as haptens, enzymes or fluorescent moieties, or other types of substances for imparting color and/or for enhancing contrast. DAB reagents can be used to provide contrast of enzyme sites (e.g., light to dark brown) and can be used to provide purple/black staining.

The receptors 11 are configured to receive and hold the dispensers 12 and can be equally spaced in a circular pattern that is axially concentric with the carousel axis 7. The number of receptors 11 can be sufficient to accommodate the number of different reagent fluid dispensers 12 required for a cycle or series of cycles. Twenty-five fluid dispenser receptors 11 are shown, but the number can be smaller or greater, and the diameter of the reagent tray 10 can be increased to accept a larger number of reagent fluid dispensers 12. A motor 14 (e.g., a stepper motor) moves a drive belt 16 to rotate the reagent carousel 8. An actuator mechanism 21 can be an air cylinder actuator that causes dispensing of fluid from one of the dispensers 12. In some embodiments, actuator mechanism 21 presses down on one of the caps of the dispensers as discussed in connection with FIGS. 9A and 9B.

The intermediate section 4 includes a vortex mixing plate to which four of the six mix blocks are attached. The remaining two mix blocks are mounted on the platform mechanism 6. Other types of mixing apparatuses can also be used.

The platform assembly 6 includes a support plate 22 upon which a slide carousel 24 is rotatably mounted. The slide carousel 24 carries the slide supports 26. Heated air is supplied by a resistive heating element and a blower. The support plate 22 also supports a controller in the form of a remote device microcontroller 36, a power supply 42, and fluid and pneumatic valves 62.

Spray blocks 60 can apply liquids such as rinses, LIQUID COVERSLIP™, etc. The remote device microcontroller 36 can include one or more processors and can be replaced by a standard computer. The remote device microcontroller 36 interfaces, via an RS-485 line, with the host device 32. The platform assembly 6 includes a support plate 40 supporting accessories, such as the power supply 42 and a buffer heater 44.

The platform 6 further includes a motor 48 (e.g., a stepper motor) that moves a drive belt 25 which in turn engages a drive sprocket of the slide carousel 24. The motor 48 can controllably rotate the slide carousel 24 to position slides under dispensers. An annular waste liquid sump surrounds the shroud and is supported on the bottom of plate 22. The waste reagent and rinse fluids are collected in the sump and passed to a drain through an outlet tube in the sump bottom.

Figure 3:
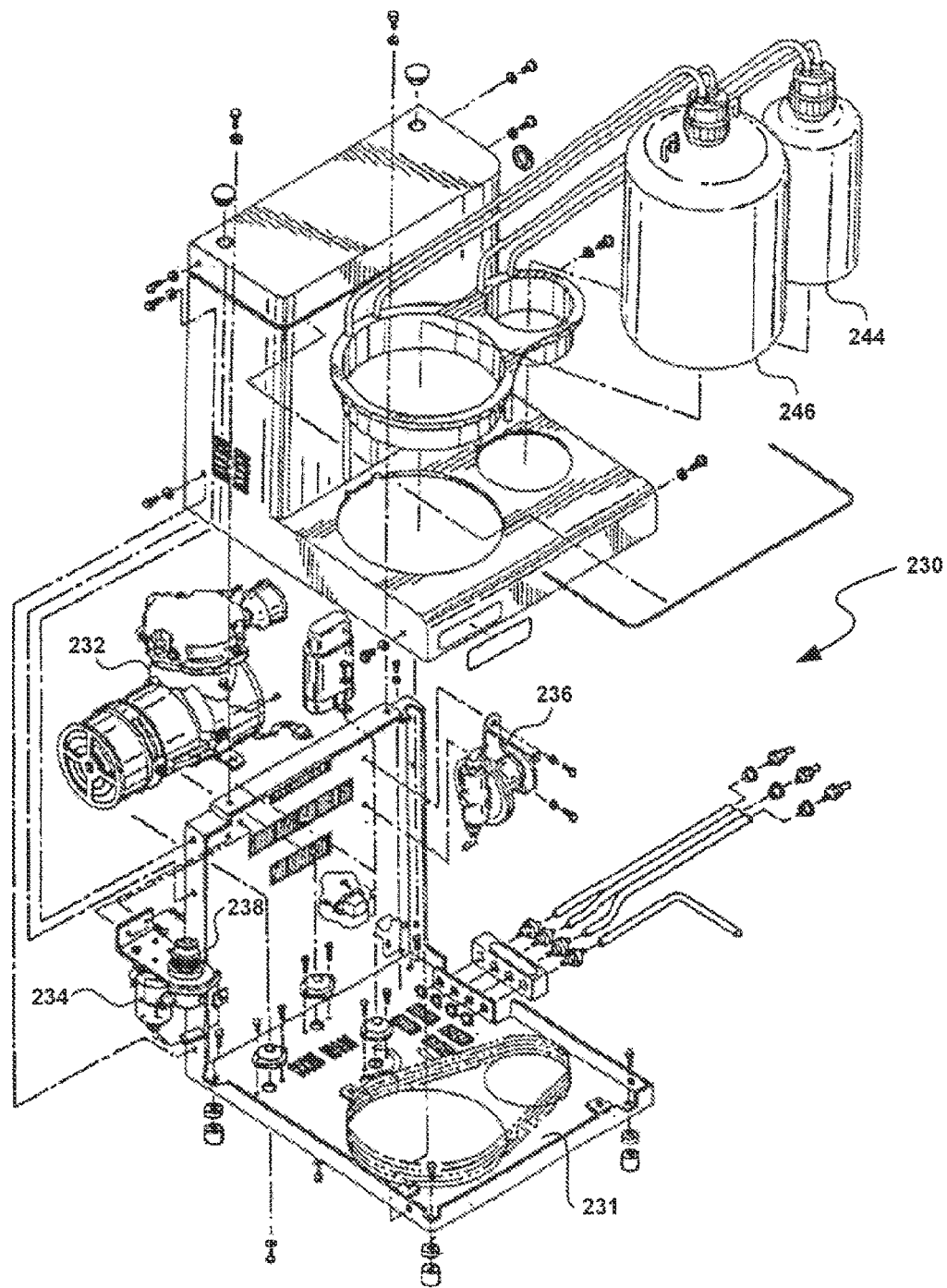
FIG. 3 is a partial exploded isometric view of a bulk fluid module according to one embodiment.

Referring to FIG. 3, bulk fluid module 230 includes an air compressor 232, a pressure relief valve 238, cooling tubing 231, a water condenser and filter 234, an air pressure regulator 236, a container 246 holding wash buffer, and a container 244 holding a coverslipping material, such as LIQUID COVERSLIP™. The air compressor 232 outputs compressed air regulated by the pressure relief valve 238 to a desired pressure (e.g., about 25 psi). The air passes from the compressor 232 through the cooling tubing 231 and enters the condenser and filter 234. From the condenser and filter 234, the air passes to the pressure regulator 236. The pressure regulator 236 regulates the pressure to a lower pressure (e.g., 13 psi). The low pressure air is supplied to the wash buffer container 246, container 44 and staining module 167. Water condensing out of the compressed air passes out of the condenser and filter through the pressure relief valve and exits the bulk module 230.

Figure 4:
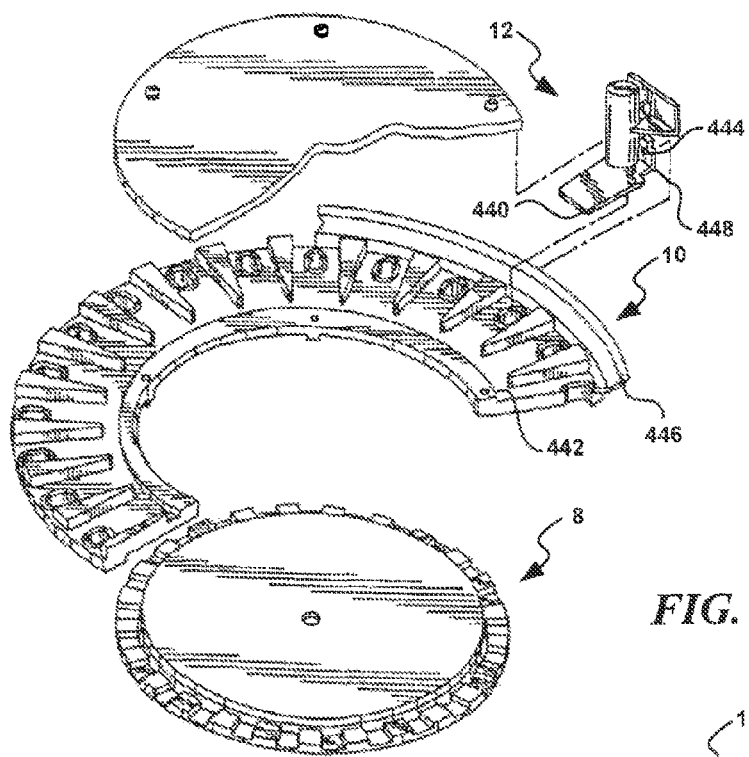
FIG. 4 is an exploded isometric view of a dispensing tray assembly.
Figure 5:
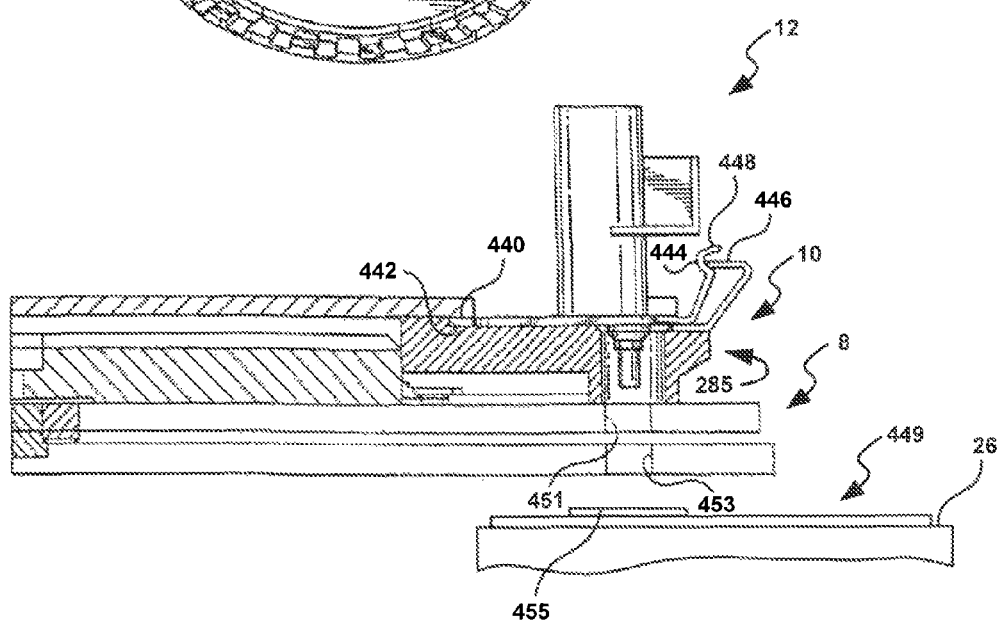
FIG. 5 is a partial cross-sectional view of a reagent tray carrying a dispenser and engaging a drive carousel.

FIGS. 4 and 5 illustrate a method of mounting a fluid dispenser 12 in a reagent tray 10. A foot 440 can be inserted into a circular U-shaped groove 442 formed in the reagent tray 10. In an alternative embodiment, the foot is inserted into a rectangular shaped groove. Groove 444 of spring member 448 engages a circumferential lip 446 of the reagent tray 10.

FIG. 5 is a cross-sectional view of the reagent tray 10 after the dispenser 12 has been mounted such that the foot 440 fits into groove 442. Fluid can fall through openings 451, 453 onto a specimen 455 on a slide 449 resting on a slide support 26. The spring member 448 flexes to hold the fluid dispenser 12 firmly in place. To remove the fluid dispenser 12, spring member 448 is simply bent inward slightly so that the groove 444 clears the lip 446, and the foot 440 is withdrawn from the groove 442. A user can conveniently remove the fluid dispenser 12 from the tray 10 to inspect, repair, refill, or replace the dispenser 12.

Figure 6:
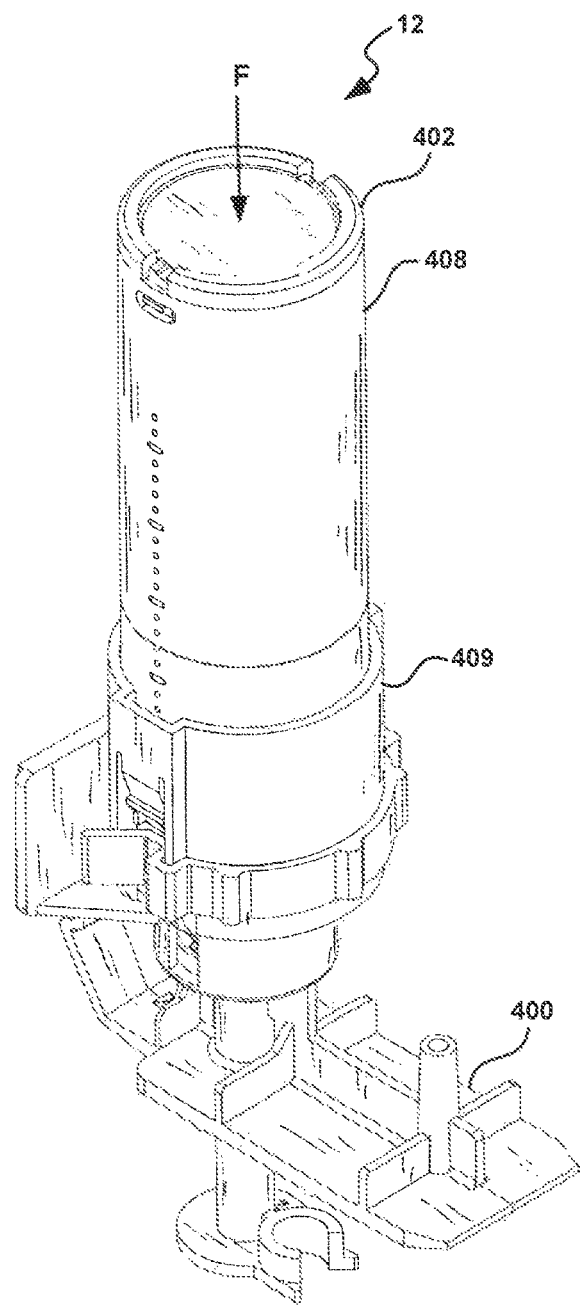
FIG. 6 is an isometric view of a dispenser according to one embodiment.
Figure 7:
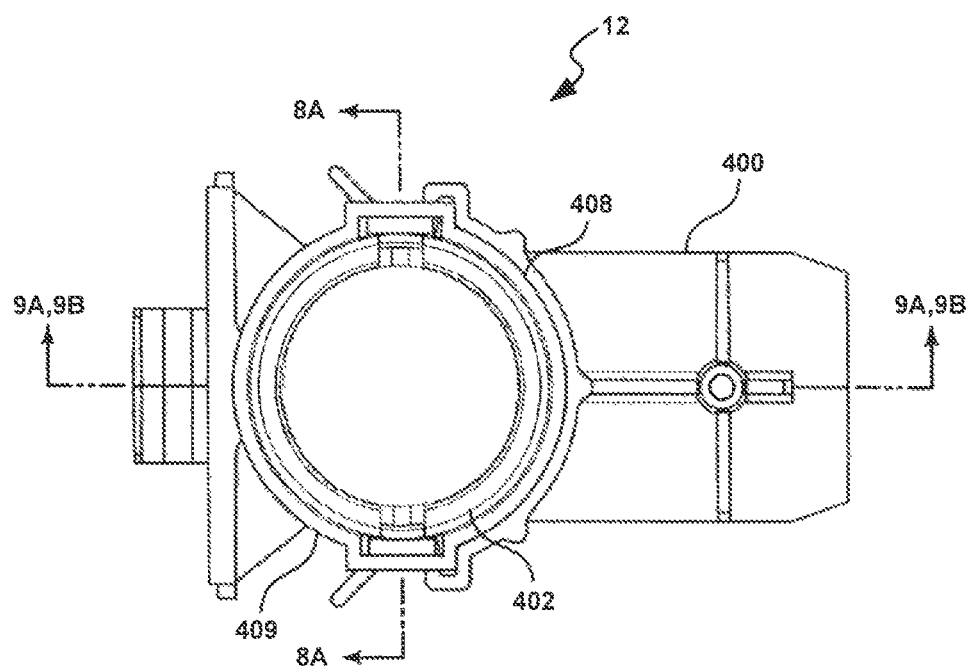
FIG. 7 is a top plan view of the dispenser of FIG. 6.

Referring to FIGS. 6 and 7, dispenser 12 includes a cap 402, a barrel 408, and a barrel holder 409. To dispense fluid, a force F (see FIG. 6) is applied to the cap 402. The barrel 408 slides into the barrel holder 409 towards a lowered or depressed position to release a predetermined volume of fluid. An actuation mechanism can return the barrel 408 to the illustrated raised or extended position. The barrel 408 can be reciprocated any number of times until it is empty. The empty dispenser 12 can be conveniently replaced with a full dispenser. In disposable embodiments, the empty dispenser 12 is discarded. In re-usable embodiments, the dispenser 12 is refilled.

Figure 8A:
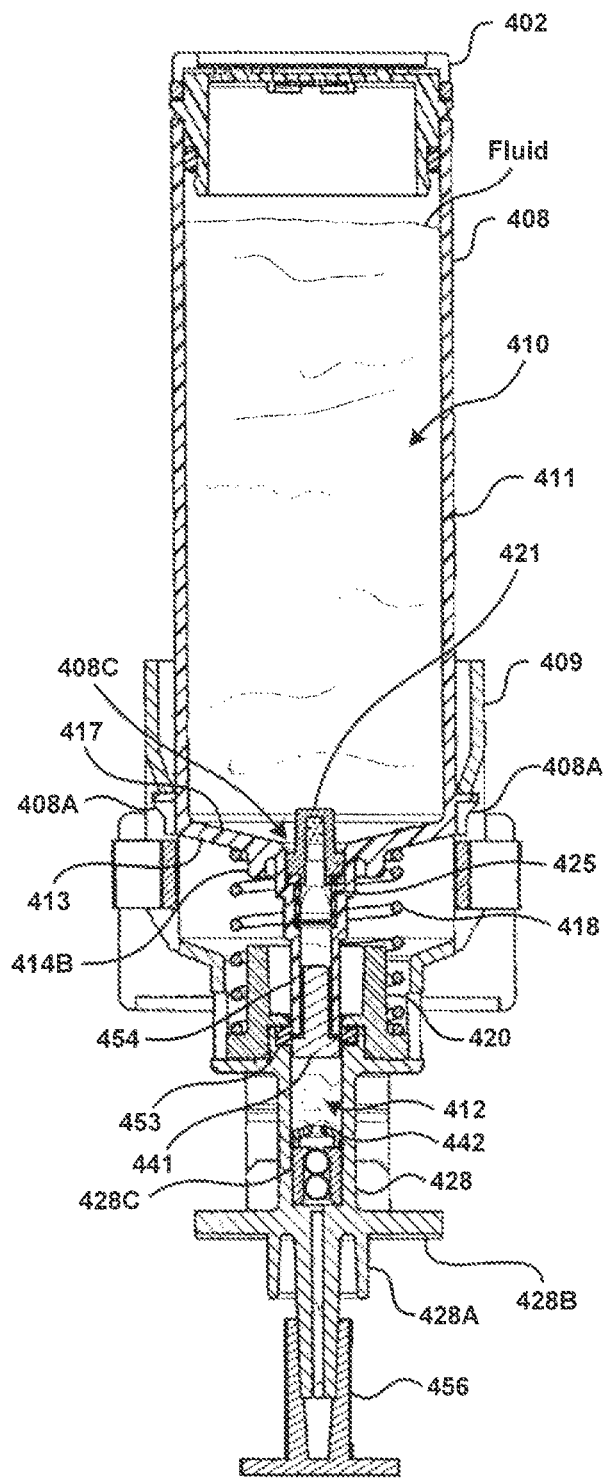
FIG. 8A is a cross-sectional view of the dispenser taken along a line 8A-8A of FIG. 7 with a barrel in a raised position.
Figure 8B:
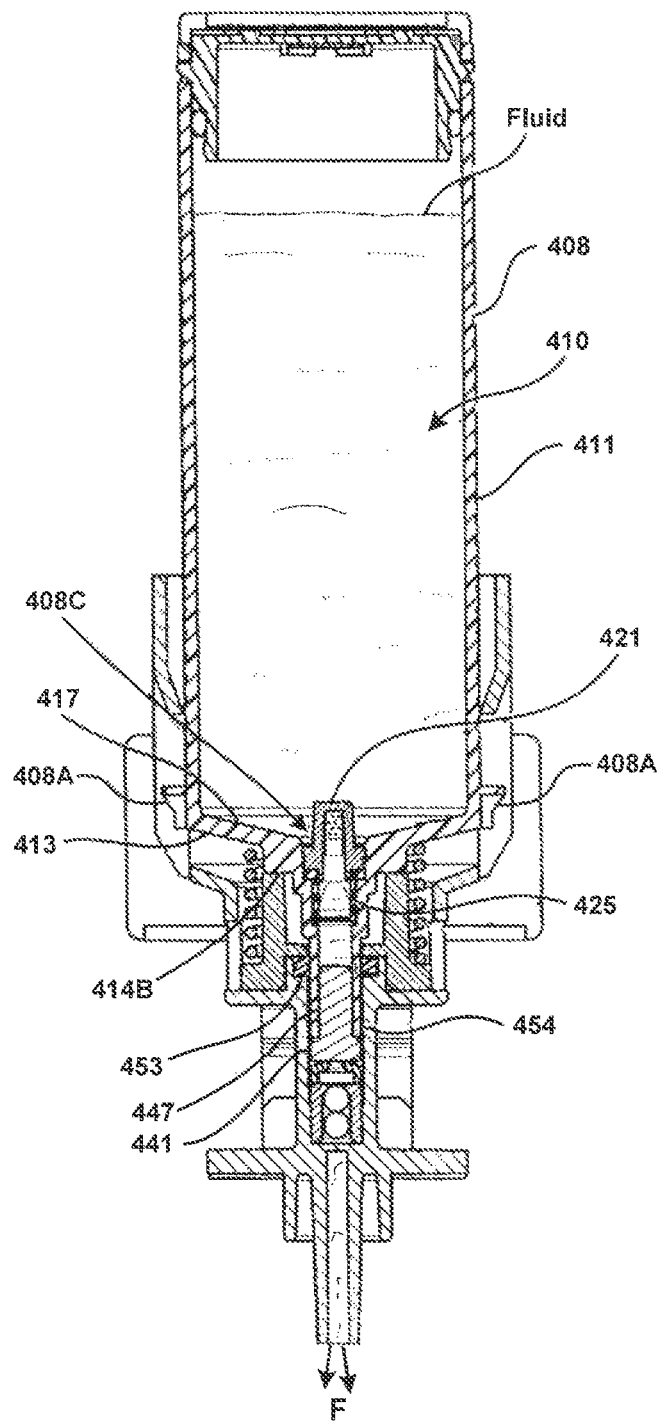
FIG. 8B is a cross-sectional view of the dispenser taken along a line 8A-8A of FIG. 7 with the barrel in a lowered position.

FIGS. 8A and 8B show the barrel 408 that includes a main body 411 defining a reservoir chamber 410. The shape of the reservoir chamber 410 can be cylindrical, funnel-shaped, or any other shape which facilitates draining of fluid through components (e.g., one or more filter devices, valves, pressure differential devices, etc.) between the reservoir chamber 410 and a dispense chamber 412. A bottom 413 of the main body 411 has a surface 417 that slopes downwardly towards a filter device 421. A valve 425 is between the reservoir 410 and the dispense chamber 412. A sealing member 453 (e.g., an O-ring, a rubber member, a quad seal, etc.) forms a fluid-tight seal with the outer surface of a piston 454. A piston head 441 has a rod 447 slideably retained in the piston 454.

Figure 9A:
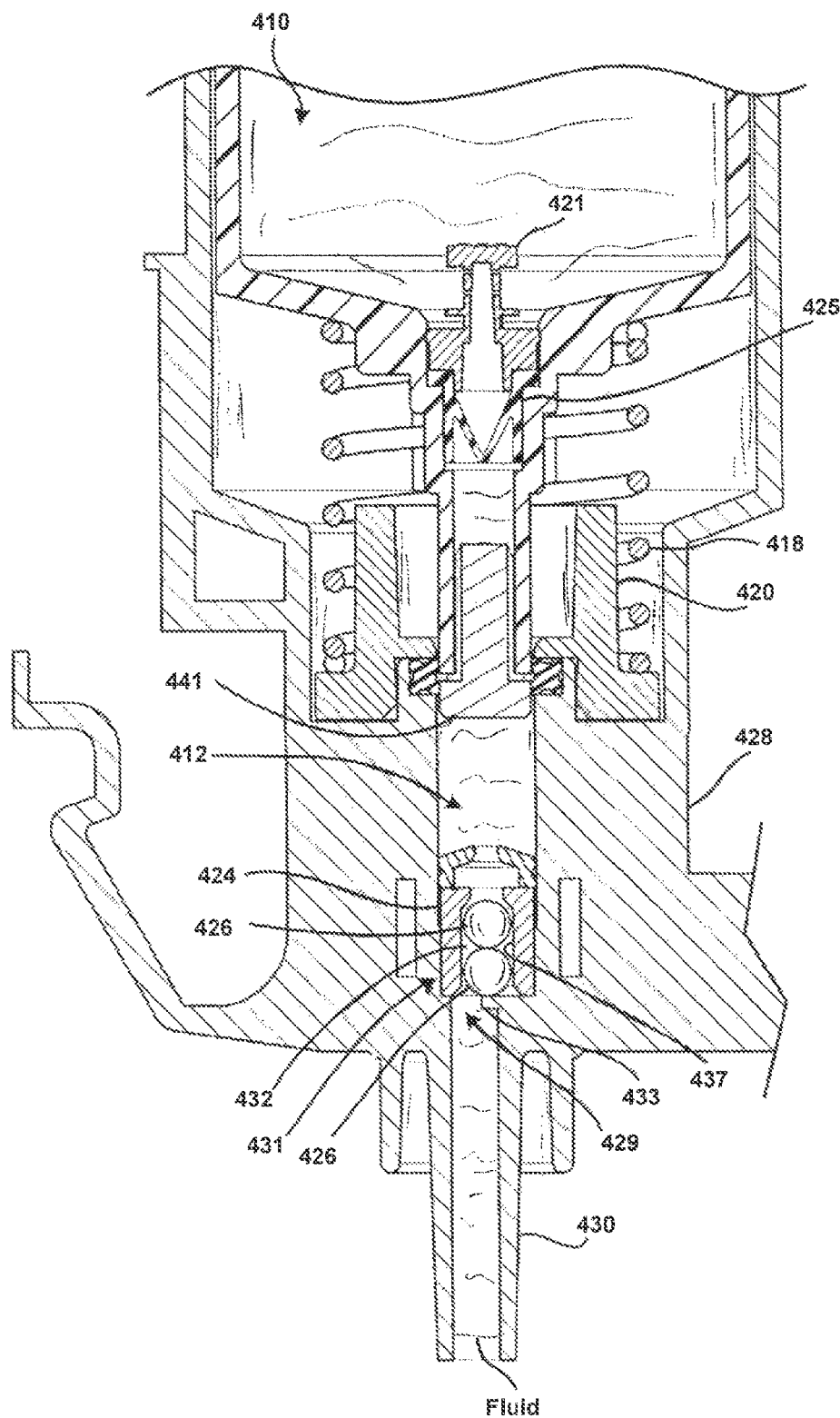
FIG. 9A is a cross-sectional view of the dispenser taken along a line 9A-9A of FIG. 7 with the barrel in the raised position.

Referring to FIG. 9A, a valve 431 includes a ball chamber 432 and is positioned upstream of a nozzle 430. A coupler 428 defines a hole 429 offset with the ball chamber 432. Ball chamber 432 contains one or more balls 426 two balls illustrated) configured to fit loosely against the cylindrical surface 437 defining the ball chamber 432. The balls 426 move freely between an uppermost position and a lowermost position. In the uppermost position (illustrated in FIG. 9B), the upper ball 426 mates with an upper end of a ball check valve insert 424, thereby preventing fluid flow towards the reservoir chamber 410. At the lowermost position (illustrated in FIG. 9A), the lower ball 426 is restrained by an inner ledge 433 of nozzle 430 and prevented from falling into nozzle 430. Fluid in the dispense chamber 412 can flow downwardly past the balls 426 and into the nozzle 430. In alternative embodiments, valve 431 can include one or more duck bill valves, umbrella valves, or other types of one-way valves.

Fluid is ejected from the dispense chamber 412 by exerting a downward force on the cap 402. When the fluid dispenser 12 is mounted on a reagent tray 10, as discussed in connection with FIG. 5, the downward force on the cap 402 is applied by the dispense cylinder, or by some other actuators or pusher capable of moving the barrel 408. When the applied force overcomes a biasing member in the form of a compression spring 418, the extended barrel 408 of FIG. 8A is moved downwardly. The fluid flows from the dispense chamber 412 into the ball chamber 432. The closed valve 425 (see FIG. 9A) pushes the fluid through the dispense chamber 412. The valve 425 and piston head 441 cooperate to keep the back pressure sufficiently high to keep the balls 426 in contact with the edge 433 such that the fluid flows around the balls 425 and through the nozzle 430.

Figure 9B:
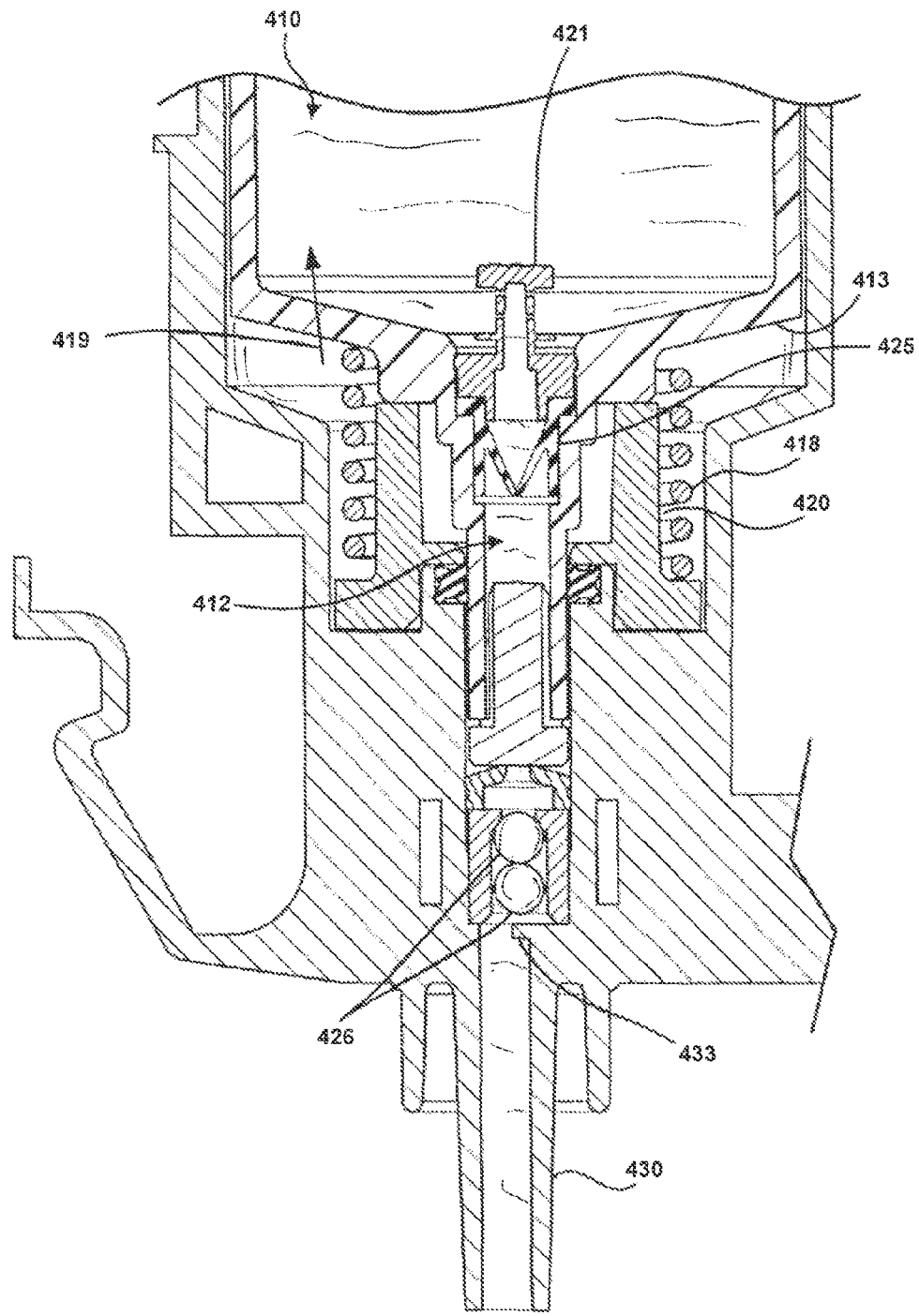
FIG. 9B is a cross-sectional view of the dispenser taken along a line 9B-9B of FIG. 7 with the barrel in the lowered position.

The barrel 408 continues to move downwardly until it reaches a stop 420, as shown in FIG. 9B. The change in volume of the dispensing chamber 412 generally corresponds to the total volume of the dispensed fluid. In some embodiments, the volume of the dispense chamber 412 is reduced causing a predetermined volume of liquid (e.g., a volume equal to approximately 50 μL, 100 μL or 150 μL) to be dispensed. The volume of dispensed liquid can be equal to the liquid volume of the region that the barrel 408 moves down minus the "suck back." The suck back can be the amount of fluid that, travels past the balls 426 on the upstroke of the barrel 408 before the balls 426 shut off the fluid flow.

The dispensing chamber 412 is refilled by allowing the barrel 408 to move upwardly. FIGS. 8B and 9B show the tapered bottom 413 of the barrel 408 contacting a stop 420. The downward force on the cap 402 can be reduced or removed. Biasing, member 418 pushes the barrel 408 in an upward direction, as indicated by an arrow 419 in FIG. 9B. As the biasing member 418 expands, the barrel 408 and the balls 426 move in the upward direction. Fluid begins to be sucked from the reservoir chamber 410 into dispense chamber 412. The volume of fluid which flows from nozzle towards dispense chamber 412 ("suck back") while the balls 426 are moving from their lowermost position to their uppermost position is preselected to be a volume equal to the volume of the hanging drop left at tip at the end of the dispense cycle. Thus, the drip is effectively drawn back into nozzle 430 and an internal meniscus can form at the tip. When the upper ball 426 reaches the top of the hull check valve insert 424, it shuts off further flow from nozzle 430 into dispense chamber 412. This immediately creates a pressure differential across the valves 425, 431, thereby opening the valve 425 to cause fluid to flow from reservoir chamber 410 into the dispense chamber 412. The suction generated in dispense chamber 412 keeps the upper ball 426 firmly seated against the ball check valve insert 424 and prevents any further flow from nozzle 430.

After the compression spring 418 has forced the barrel 408 hack to the extended position of FIG. 9A, fluid dispenser 12 is ready for another dispense cycle. The balls 426 can move freely within ball chamber 432, and therefore provide essentially no resistance to fluid flow from nozzle 430 until the upper ball 426 reaches its sealing position at the ball check valve insert 424. When the pressure differential is at equilibrium, the balls 426, which are made of a material slightly more dense than the liquid, can fall through the ball chamber 432 until the lower ball 426 makes contact again with the edge 433.

Referring to FIGS. 8A and 8B, protrusions 408A help position the barrel 408 on the upstroke. If the spring 418 pushes the barrel 408 upward too high, the seal, as provided by a seal member 453, may be broken thereby creating an air path and causing the fluid dispenser 12 to lose prime. The barrel 408 also has a flange 414B which mates with the stop 420 on the downstroke. The barrel 408 also has a pocket 408C. The filter device 421 and valve 425 can be inserted into the pocket 408C. The pocket 408C acts as a funnel so that substantially no puddles are formed at the bottom of the barrel 408, thereby minimizing waste. The barrel 408 also has at its lower portion the piston 454 by which fluid is expelled in the dispenser 12. The piston 454 can be integrally formed with the main body 411 using an extruding, process, molding process (e.g., an injection molding process, blow molding process, etc.), or the like.

A nozzle cap 456 of FIG. 8A engages the nozzle 430 of the coupler 428. The nozzle cap 456 and nozzle 430 are matched using a luer fitting design in order to be a fluid tight seal.

The coupler 428 has bumps 428C of FIG. 8A in which the ball check valve insert 424 snaps. The bumps act to prevent any leakage of fluid downward or air upward through the walls of the ball check valve insert 424 and the coupler wall. The coupler 428 also has protrusions 428A, which ensure that the dispenser is aligned on the reagent tray 10. For example, if the dispenser is misaligned, the dispense cylinder may not engage the dispenser properly. The coupler also has stabilizing bumps 428B, which reduce any rocking back and forth of the fluid dispenser 12.

To assemble and fill the fluid dispenser 12, the valve 425 and filter device 421 are placed in the lower part of the barrel 408. The balls 426 are placed in the ball check valve insert 424, which is snapped into place. The seal 453 is inserted into the coupler 428. The stop 420 and biasing member 418 are inserted into the coupler 428 and the coupler 428 is snapped onto the barrel 408. The barrel 408 is filled with a substance (e.g., a reagent, rinse, buffer, etc.). The fluid dispenser 400 can be primed. The cap 402 is placed on the top of the dispenser and the nozzle cap 456 is placed on the output of the nozzle 430 on the coupler 428. U.S. application Ser. No. 10/913,932 discloses methods of manufacturing various components of the fluid dispenser. It is noted that the filter device 421 can be made, in whole or in part, of polypropylene or other polymers suitable for contacting the subject to be dispensed.

Figure 10:
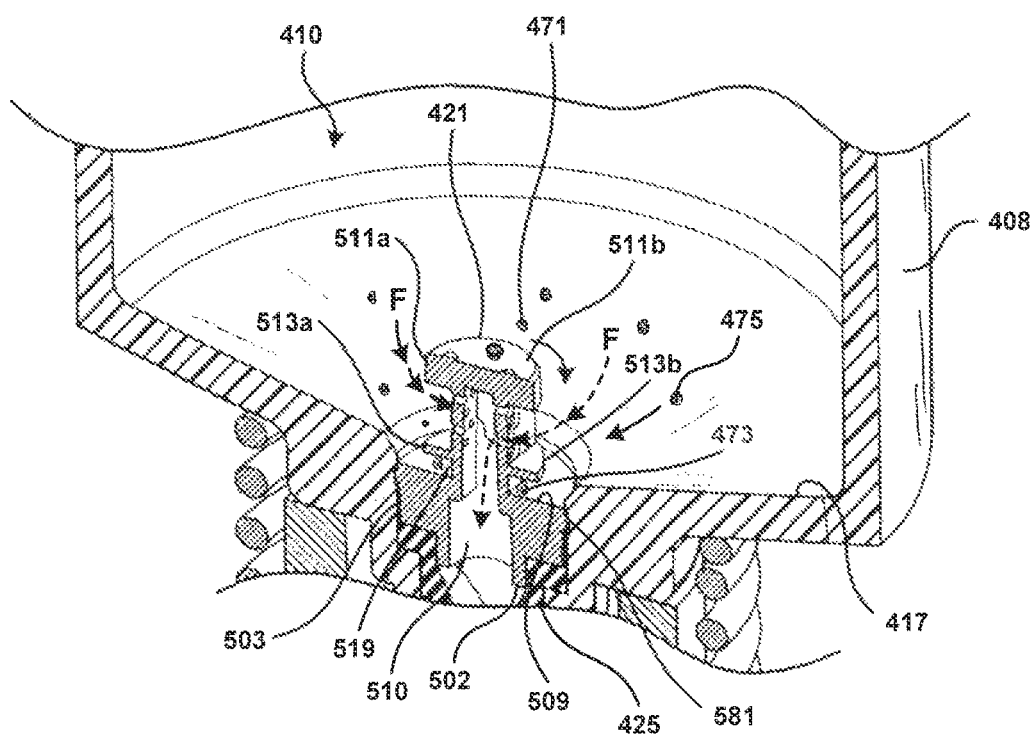
FIG. 10 is a detailed cross-sectional view of a barrel and a filter device, according to one embodiment.

FIG. 10 is a cross-sectional view of the filter device 421. The filter device 421 is configured to allow fluid, represented by arrows, to pass towards the downstream valve 425 while substantially blocking large solid particles. In some embodiments, filtrate exiting the filter device 421 can be substantially free from particles (e.g., contaminates, precipitate, or other solid particles) that would tend to cause malfunctioning or improper specimen processing. Filtrate can be a substantially precipitate-free filtrate which can be a fluid with substantially no solid particles having an outer diameter equal to or greater than a predetermine size (e.g., a diameter of about 0.01 inch). Most or all of the solid particles of the predetermined size are therefore kept in the reservoir chamber 410. A base 502 includes a bead 581 configured to provide an interference fit neck region 503 of the barrel 408. The filter device 421 is positioned at the lowest region of the reservoir chamber 410 such that particles (e.g., particle 475) tend to travel down a sloped surface 417 and collect along an upper surface 509 of the base 502.

Figure 11:
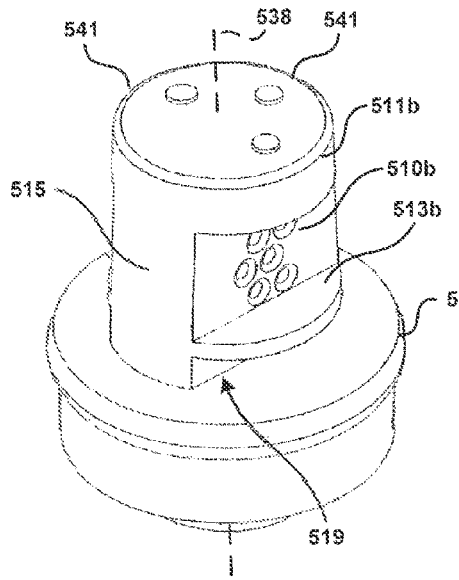
FIG. 11 is an isometric view of a filter device according to one embodiment.
Figure 12:
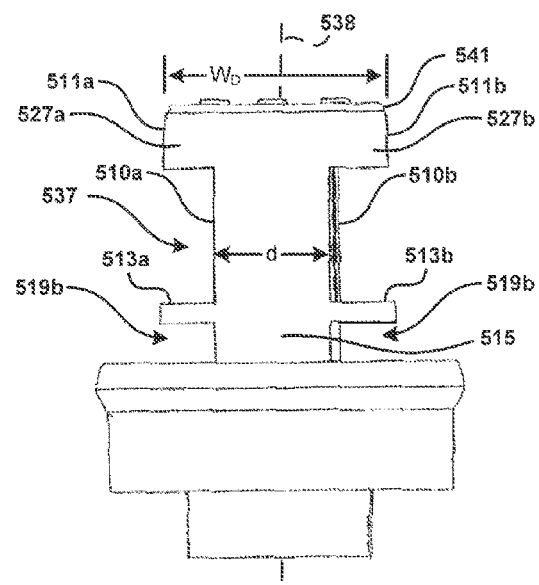
FIG. 12 is a front elevational view of the filter device of FIG. 11.

Referring to FIGS. 10-12, anti-clogging elements 511a, 511b, 513a, 513b cooperate to keep particles away from filtering elements 510a, 510b while fluid flows through substantially horizontally oriented flow channel 537 to access the filtering element 510b. The anti-clogging element 513a is in the form of a collection rib coupled to a main body 515. As shown in FIG. 10, particle 475 can move downwardly along the sloped surface 417 and into a particle collection gap 519b (see FIG. 12). The collection rib 513b obstructs upward movement of the particle 473 to keep the particle 473 from being carried (e.g., by circulating fluid) immediately adjacent to the filtering element 510b. When fluid circulates in the reservoir chamber 410, particle 473 tends to remain below the collection rib 513.

Figure 13:
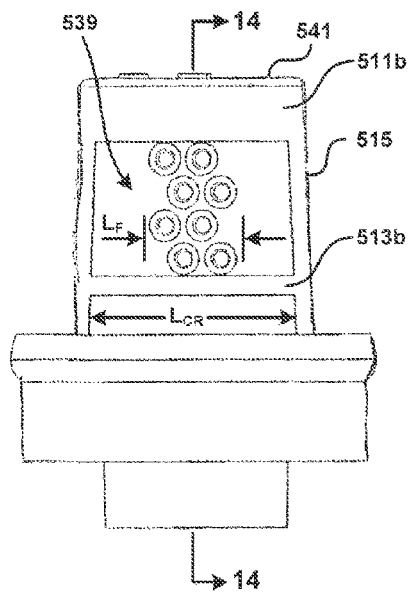
FIG. 13 is a side elevational view of the filter device of FIG. 11.
Figure 14:
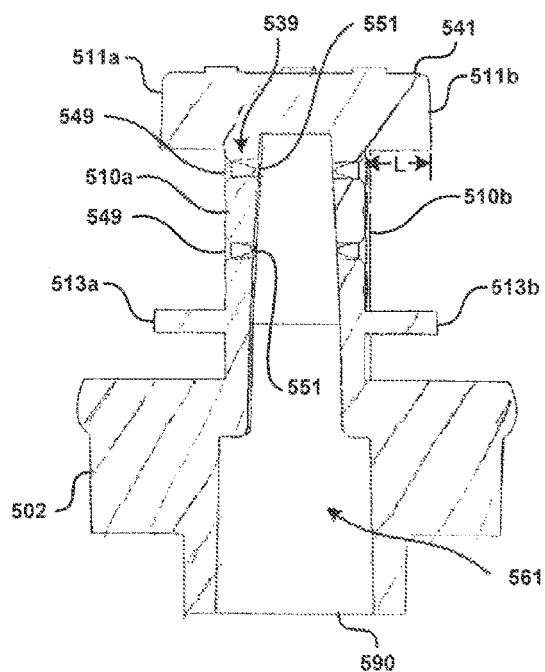
FIG. 14 is a cross-sectional view of the filter device taken along a line 14-14 of FIG. 13.

In some embodiments, including the illustrated embodiment of FIGS. 12 and 14, collection ribs 513a, 513b are horizontally oriented arcuate shaped flanges that protrude outwardly away from a longitudinal axis 538 of the filter device 421. Inlets 549 of through-holes 539 are closer to the longitudinal axis 538 than the outer peripheries of collection ribs 513a, 513b. The length $L_{CR}$ of the collection ribs 513a, 513b can be longer than a length $L_F$ defined by a perforated region of an adjacent filtering element 510a, 510b, as shown in FIG. 13.

Anti-clogging elements 511a, 511b help keep particles travelling downwardly through the chamber 410 from travelling directly in front of the filtering elements 510a, 510b. The particle 471 of FIG. 10 can travel downwardly past the anti-clogging element 511b due to gravity, but is kept spaced well apart from the filtering element 510b. In some embodiments, including the embodiment illustrated in FIGS. 11-14, anti-clogging elements 511a, 511b are formed by a circular disk 541 integrally formed with the main body 515. The elements 511a, 511b are substantially parallel to the collection ribs 513a, 513b, respectively. A width $W_D$ of the disk 541 (see FIG. 12) is substantially greater that a distance d defined by the exterior of the filtering elements 510a, 510b. Particles tend to not reach the filtering elements 510a, 510b because fluid has to flow generally horizontally beneath the elements 511a, 511b, illustrated as protruding cantilevered arcuate members. Outer peripheries 527a, 527b of the elements 511a, 511b are further away from the longitudinal axis 538 than the inlets 549.

Filtering elements 510a, 510b can be similar to one another, and accordingly, the description of one applies equally to the other, unless clearly indicated otherwise. As shown in FIG. 14, filtering element 510a is in the form of a perforated wall with through holes 539. Inlets 549 of the through holes 539 face outwardly. Outlets 551 of the through holes 549 face a hollow region or lumen 561. Fluid flows through the lumen 561 and exits an outlet port 590.

The through-holes 539 can be dimensioned to prevent the passage of particles having an outer diameter equal to or larger than a threshold size. The threshold size can be selected based on the design of downstream components. For example, if particles with an outer dimension (e.g., a diameter) longer than about 0.01 inch tend to cause malfunctioning of downstream components, the threshold size can be equal to about 0.01 inch. In such embodiments, through-holes 539 have a diameter equal to or smaller than about 0.01 inch and can be conveniently manufactured using molding processes, such as injection molding processes. In other embodiments, through-holes 539 can have diameters equal to or smaller than about 0.005 inch or 0.001 inch and can be formed by a multi-stage molding or machining process. The filtering elements 510a, 510b can also be configured to block particles having cross-sectional areas that are substantially less than a minimum flow area of the lumen 561.

Filtering elements can also include one or more screens, meshes, filter papers, membranes (e.g., permeable membranes, semi-permeable membranes, porous membranes, etc), bed of media (e.g., a bed of material that retains solid particles), cloth, combinations thereof, or other types of filtering elements capable of blocking, trapping, or otherwise retaining particles. If the submerged filtering element tends to promote nucleation and subsequent precipitation of relatively large solid particles, multiple filtering elements can be employed to ensure that precipitates are trapped.

Figure 15:
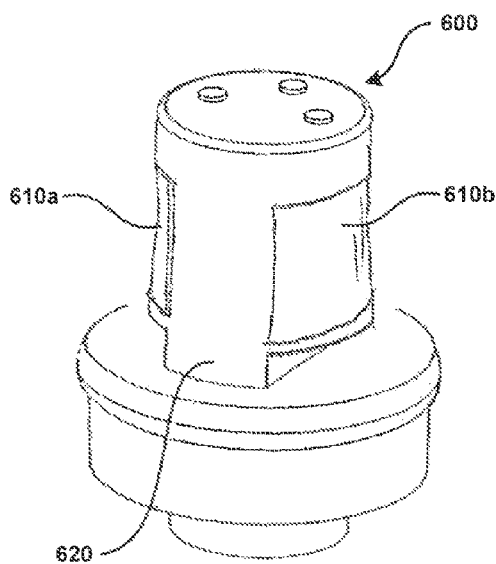
FIG. 15 is an isometric view of a filter device according to one embodiment.
Figure 16:
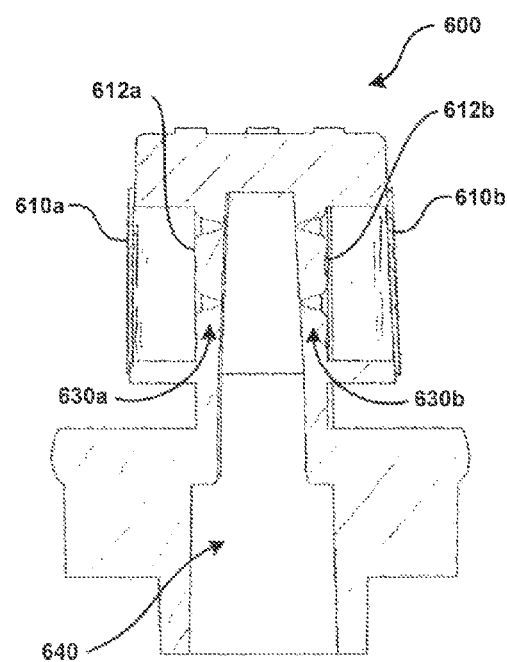
FIG. 16 is a cross-sectional view of the filter device of FIG. 15.

FIGS. 15 and 16 show a filter device that is similar to the filter device 421 of FIGS. 11-14 except as detailed below. The filter device 600 includes filtering elements 610a, 610b (collectively "610") in the form of screens or meshes and inner filtering elements 612a, 612b (collectively "612") in the form of perforated sidewalls of a main body 620. The outer filtering elements 610a, 610b can help keep particles from reaching the perforated sidewalk 612a, 612b. If small particles make it past the filtering elements 610a, 610b, through holes 630a, 630b can be dimensioned to block particles from entering a central lumen 640. During use, particles can become trapped between the outer and inner filtering elements 610a, 610b, 612a, 612b.

A wide range of different types of filtering configurations can be used. For example, filter elements 610a, 610b can be the only elements (e.g., filtration elements 612a, 612b may not be present). Additionally, a filter device may comprise different outer portions that may have different types of filtering elements. For example, one section of a tubular or tower shaped filter device can have a sidewall defined by the filter elements 610 while another portion of the sidewall is defined by flat or curved filter elements 612. In one embodiment, an upper portion of a sidewall can have an annular or tubular screen or mesh 610. A lower portion of the sidewall can have a tubular perforated region 610 below the screen or mesh 610.

The embodiments, components, features, systems, devices, methods and techniques described herein may, in some embodiments, be similar to any one or more of the embodiments, features, systems, devices, materials, methods and techniques described in U.S. application Ser. No. 10/913, 932 (U.S. Pub. No. 2005/0135972), which is incorporated herein by reference in its entirety. By way of example, filtering elements disclosed herein can be incorporated into the dispensers illustrated in FIGS. 12A-15C, 17A-18B, and 20 of U.S. application Ser. No. 10/913,932, in addition, the embodiments, features, systems, devices, methods and techniques described herein may, in certain embodiments, be applied to or used in connection with any one or more of the embodiments, features, systems, devices, materials, methods and techniques disclosed in the above-mentioned U.S. application Ser. No. 10/913,932. U.S. Pat. Nos. 5,418,138; 6,045, 759; 6,192,945; and 6,416,713 are also herein by reference in their entireties. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A fluid dispenser for a biological sample processing system, the fluid dispenser comprising:
   a barrel including a main body and a piston coupled to the main body, the main body including a sidewall and a bottom that at least partially define a reservoir chamber for holding fluid;
   a valve positioned downstream of the reservoir chamber; and
   a filter device upstream of the valve and including a protective cantilevered member and a vertically oriented filtering element having a plurality of through-holes with inlets positioned closer to a longitudinal axis of the filter device than an outer periphery of protective cantilevered member positioned above the plurality of through-holes, wherein the filtering element extends upwardly through at least a portion of the reservoir chamber when the barrel is in a vertical orientation to allow the fluid, which is in the reservoir chamber and located between the filtering element and the sidewall of the main body, to pass laterally through the filtering element and to flow towards the valve while the filtering element substantially blocks precipitates in the fluid having a threshold size.

2. The fluid dispenser of claim 1, wherein the valve is positioned in the barrel and another valve is positioned downstream of the barrel, the filtering element configured to block precipitates sufficiently large to cause malfunctioning of at least one of the valve positioned in the barrel and the valve positioned downstream of the barrel.

3. The fluid dispenser of claim 1, wherein the filter device includes at least one anti-clogging element configured to keep precipitates, which are in the reservoir chamber, away from the filtering element of the filter device.

4. The fluid dispenser of claim 3, wherein the filter device includes a hollow main body with a flow lumen and an outlet port, and wherein the at least one anti-clogging element includes a particle blocking member that extends outwardly from the hollow main body beyond the filtering element of the filter device.

5. The fluid dispenser of claim 1, wherein the filter device includes a protrusion that extends towards the sidewall of the main body so as to obstruct precipitates moving vertically through the fluid generally toward the inlets.

6. The fluid dispenser of claim 1, wherein the filter device includes a collector rib extending laterally outward from a main body of the filtering element, the collector rib configured to block particles below the collector rib from moving upwardly towards the filtering element.

7. The fluid dispenser of claim 1, wherein the filter device is positioned at a bottom of the reservoir chamber, the filter device further comprises a main body that extends upwardly partially through the reservoir chamber, and the filtering element is positioned along a sidewall of the main body of the filter device.

8. The fluid dispenser of claim 1, wherein the filtering element is configured to substantially block precipitates having outer diameters equal to about 0.01 inch.

9. The fluid dispenser of claim 1, wherein the filtering element includes a pair of spaced apart perforated sidewalls that allow fluid flow into and through an interior region of the filtering device.

10. The fluid dispenser of claim 1, wherein the filtering element includes a vertical sidewall through which the plurality of through-holes extends, wherein the vertical sidewall is spaced apart from the sidewall of the main body such that fluid directly between the vertical sidewall of the filtering element and the sidewall of the main body flows horizontally through the through-holes.

11. A biological processing system, comprising:
    a platform assembly including a plurality of slide holders; and
    a dispenser assembly including a plurality of dispensers, the platform assembly and the dispenser assembly configured to cooperate to sequentially position the dispensers relative to specimen-bearing slides on the slide holders to enable dispensing of substances onto the specimen-bearing slides, wherein at least one of the dispensers includes a filter device for filtering a substance to deliver a substantially precipitate-free filtrate through a valve and onto one of the specimen-bearing slides, the filter device including
    a protective cantilevered member, and
    a vertically oriented sidewall including plurality of through-holes with inlets positioned closer to a longitudinal axis of the filter device than an outer periphery of the protective cantilevered member positioned above or below the plurality of through-holes.

12. The biological processing system of claim 11, wherein the at least one dispenser comprises:
   a barrel holder including a biasing member and an outlet; and
   a barrel guided within the barrel holder, the barrel including a main body and a piston coupled to the main body, the main body defining a reservoir chamber for holding a fluid, wherein the sidewall is perforated to allow fluids in the reservoir chamber to pass therethrough while substantially blocking precipitates of a threshold size from exiting the barrel.

13. The biological processing system of claim 11, wherein the plurality of dispensers contain fluids for performing at least one staining protocol, and the at least one dispenser contains a DAB reagent.

14. The biological processing system of claim 11, wherein the sidewall is configured to substantially block precipitates in a chamber of the at least one dispenser while allowing the substance to flow into an interior chamber of the filter device.

15. The biological processing system of claim 11, wherein the sidewall extends upwardly through at least a portion of a reservoir chamber of the at least one dispenser to allow the substance in the reservoir chamber to flow horizontally through the through-holes and to flow vertically through the valve.

16. A fluid dispenser for a biological sample processing system, the fluid dispenser comprising:
   a barrel including a main body and a piston coupled to the main body, the main body including a sidewall and a bottom at least partially defining a reservoir chamber for holding fluid;
   a valve; and
   a filter device positioned upstream of the valve and including a vertically oriented filtering element having a plurality of through-holes, wherein the filtering element extends upwardly through at least a portion of the reservoir chamber and is spaced apart from the sidewall of the main body such that fluid located directly between the filtering element and the sidewall of the main body flows laterally through the through-holes when the barrel is in a generally vertical orientation.

17. The fluid dispenser of claim 16, wherein the filter device includes at least one anti-clogging element positioned beneath the filtering element, wherein the anti-clogging element is configured to keep precipitates, which are at a bottom of the reservoir chamber, from traveling upwardly towards the filtering element.

18. The fluid dispenser of claim 17, wherein the at least one anti-clogging element includes a collector rib that extends laterally outward from a main body of the filter device.

19. The fluid dispenser of claim 16, wherein the filter device includes a protective cantilevered member extending laterally outward from a main body of the filter device such that the protective cantilevered member blocks particles, which are located in the reservoir chamber, from moving vertically towards the filtering element.

20. The fluid dispenser of claim 16, wherein the filter device further comprises:
   an anti-clogging element that extends laterally outward beyond the filtering element such that the anti-clogging element is located above the bottom of the barrel to block particles in fluid traveling upward away from the bottom of the barrel; and
   a protrusion that extends laterally outward beyond the filtering element and towards a sidewall of the barrel so as to obstruct precipitates moving downward through the fluid generally toward the inlets.

21. The fluid dispenser of claim 16, wherein the filtering element is a first filtering element, and wherein the filter device further comprises
   a second filtering element, and
   an interior chamber, wherein the second filter element extends vertically through at least a portion of the reservoir chamber, and wherein the interior chamber is located between the first and second filtering elements.

22. The fluid dispenser of claim 21, wherein each of the first and second filtering elements is a perforated vertical wall.

23. The fluid dispenser of claim 16, wherein the filtering device includes an upper particle blocking member and a lower particle blocking member, the upper particle blocking member and the lower particle blocking member protruding outwardly from the main body to define a substantially horizontal flow channel through which fluid is capable of flowing to access the at least one filtering element.

* * * * *